United States Patent
Font Freide et al.

(10) Patent No.: US 6,822,005 B2
(45) Date of Patent: Nov. 23, 2004

(54) FISCHER-TROPSCH PROCESS

(75) Inventors: Josephus Johannes Helena Maria Font Freide, Guildford (GB); John Richard Hensman, Hertfordshire (GB); David Newton, Surrey (GB); Christopher Sharp, Staines (GB); Geoffrey Benedict Smith, Surrey (GB)

(73) Assignees: BP Exploration Operating Company Limited, London (GB); Davy Process Technology Limited, London (GB)

(*) Notice: Subject to any disclaimer, the term of this patent is extended or adjusted under 35 U.S.C. 154(b) by 0 days.

(21) Appl. No.: 10/476,625

(22) PCT Filed: May 17, 2002

(86) PCT No.: PCT/GB02/02332
§ 371 (c)(1),
(2), (4) Date: Nov. 3, 2003

(87) PCT Pub. No.: WO02/096837
PCT Pub. Date: Dec. 5, 2002

(65) Prior Publication Data

US 2004/0132836 A1 Jul. 8, 2004

(30) Foreign Application Priority Data

| May 25, 2001 | (GB) | ............................................. | 0112787 |
| May 25, 2001 | (GB) | ............................................. | 0112788 |
| May 25, 2001 | (GB) | ............................................. | 0112795 |
| May 25, 2001 | (GB) | ............................................. | 0112798 |
| Jun. 6, 2001 | (GB) | ............................................. | 0113786 |

(51) Int. Cl.$^7$ .............................................. C07C 27/00
(52) U.S. Cl. ........................ 518/712; 518/700; 518/705
(58) Field of Search ............................... 518/700, 705, 518/712

(56) References Cited

FOREIGN PATENT DOCUMENTS

| GB | 728543 A | 4/1955 |
| WO | WO 01/38269 A1 | 5/2001 |

*Primary Examiner*—J. Parsa
(74) *Attorney, Agent, or Firm*—Nixon & Vanderhye (57) ABSTRACT

A process for the conversion of synthesis gas to hydrocarbons by contacting the synthesis gas at an elevated temperature and pressure with a suspension comprising a solid particulate catalyst suspended in a liquid medium, which contacting takes place in a system comprising at least one high shear mixing zone and a reactor vessel wherein the volume of suspension present in the high shear mixing zone(s) is substantially less than the volume of suspension present in the reactor vessel, suspension is mixed with synthesis gas in the high shear mixing zone(s), the resulting mixture of suspension and synthesis gas is discharged from the high shear mixing zone(s) into the reactor vessel and wherein kinetic energy is dissipated to the suspension present in the high shear mixing zone(s) at a rate of at least 0.5 kW/m$^3$ relative to the total volume of suspension present in the system.

48 Claims, 1 Drawing Sheet

FISCHER-TROPSCH PROCESS

This application is the U.S. National Phase of International Application PCT/GB 02/02332, filed 17 May 2002, which designated the U.S.

The present invention relates to a process for the conversion of carbon monoxide and hydrogen (synthesis gas) to liquid hydrocarbon products in the presence of a Fischer-Tropsch catalyst.

BACKGROUND OF THE INVENTION

In the Fischer-Tropsch synthesis reaction a gaseous mixture of carbon monoxide and hydrogen is reacted in the presence of a catalyst to give a hydrocarbon mixture having a relatively broad molecular weight distribution. This product is predominantly straight chain hydrocarbons which typically have a chain length of more than 2 carbon atoms, for example, more than 5 carbon atoms. The reaction is highly exothermic and therefore heat removal is one of the primary constraints of all Fischer-Tropsch processes. This has directed commercial processes away from fixed bed operation to slurry systems. Such slurry systems employ a suspension of catalyst particles in a liquid medium thereby allowing both the gross temperature control and the local temperature control (in the vicinity of individual catalyst particles) to be significantly improved compared with fixed bed operation.

Fischer-Tropsch processes are known which employ slurry bubble columns in which the catalyst is primarily distributed and suspended in the slurry by the energy imparted from the synthesis gas rising from the gas distribution means at the bottom of the slurry bubble column as described in, for example, U.S. Pat. No. 5,252,613.

The Fischer-Tropsch process may also be operated by passing a stream of the liquid medium through a catalyst bed to support and disperse the catalyst, as described in U.S. Pat. No. 5,776,988. In this approach the catalyst is more uniformly dispersed throughout the liquid medium allowing improvements in the operability and productivity of the process to be obtained.

GB 728543 relates to a process for the production of hydrocarbons by the reaction of synthesis gas in the presence of a catalyst which may be suspended in finely divided form within the hydrocarbon oil (contact oil). A mechanically moved stream of contact oil circulating after the separation of the gas, and the synthesis gas is introduced into the reaction chamber below a cooling arrangement disposed therein, suitably by means of one or a series of nozzles. Cooling of the contact oil or mixture of contact oil and gas in the reaction chamber is effected in a number of stages in such manner that the mixture of synthesis gas and contact oil successively flows through cooling stages at increasing temperature. Owing to the fact that the individual cooling stages have a temperature increasing from the bottom upwards, the reaction can be retarded in places where the concentration of carbon monoxide and hydrogen is highest, namely in the lower part of the reaction tower, by the application of low temperatures. In accordance with the reduction of the concentration of the reaction substances, the temperature is then increased in the higher zones of the reaction tower, so that the complete reaction between the carbon monoxide and the hydrogen, corresponding substantially to equilibrium, is obtained in the neighborhood of the top of the reaction tower. Thus, GB 728,543 relates to a plug flow reactor vessel where the reaction conditions vary in the individual cooling stages.

SUMMARY OF THE INVENTION

We have recently found that a Fischer-Tropsch process may be operated by contacting synthesis gas with a suspension of catalyst in a liquid medium in a system comprising at least one high shear mixing zone and a reactor vessel. The suspension is passed through the high shear mixing zone(s) where synthesis gas is mixed with the suspension under conditions of high shear. The shearing forces exerted on the suspension in the high shear mixing zone(s) are sufficiently high that the synthesis gas is broken down into gas bubbles and/or irregularly shaped gas voids. Suspension having gas bubbles and/or irregularly shaped gas voids dispersed therein is then discharged from the high shear mixing zone(s) into the reactor vessel where the majority of the conversion of synthesis gas to liquid hydrocarbon products takes place. The suspension present in the reactor vessel is under such highly turbulent motion that any irregularly shaped gas voids dispersed therein are constantly coalescing and fragmenting over a rapid time frame, for example, over a period of up to 500 ms. The transient nature of these irregularly shaped gas voids results in improved heat transfer and mass transfer of gas into the liquid phase of the suspension when compared with a conventional slurry bubble column reactor. This process is described in WO 0138269 (PCT patent application number GB 0004444) which is herein incorporated by reference.

It has now been found that the catalytic conversion of synthesis gas to hydrocarbon products is improved when the kinetic energy dissipation rate in the high shear mixing zone(s) is at least 0.5 kW/m$^3$ relative to the total volume of suspension present in the system.

The present invention therefore relates to a process for the conversion of synthesis gas to hydrocarbons by contacting the synthesis gas at an elevated temperature and pressure with a suspension comprising a solid particulate Fischer-Tropsch catalyst suspended in a liquid medium, which contacting takes place in a system comprising at least one high shear mixing zone and a reactor vessel wherein the volume of suspension present in the high shear mixing zone(s) is substantially less than the volume of suspension present in the reactor vessel, suspension is mixed with synthesis gas in the high shear mixing zone(s), the resulting mixture of suspension and synthesis gas is discharged from the high shear mixing zone(s) into the reactor vessel and wherein kinetic energy is dissipated to the suspension present in the high shear mixing zone(s) at a rate of at least 0.5 kW/m$^3$ relative to the total volume of suspension present in the system.

For avoidance of doubt, the conversion of synthesis gas to hydrocarbons is initiated in the high shear mixing zone(s) although the majority of the conversion generally occurs in the reactor vessel.

Without wishing to be bound by any theory it is believed that when kinetic energy is dissipated to the suspension present in the high shear mixing zone(s) at a rate of at least 0.5 kW/m$^3$ relative to the total volume of suspension present in the system, the rate of mass transfer of synthesis gas to the suspension is enhanced. Suitably, in the process of the present invention, the volumetric mass transfer rate is in the range 2 to 10,000, preferably, 25 to 1000, more preferably 5 to 100 kg-moles/h of carbon monoxide transferred per m$^3$ of suspension. Suitably, in the process of the present invention, the mass transfer rate is in the range $5 \times 10^{-3}$ to $5 \times 10^{-6}$ kg-moles carbon monoxide transferred per m$^2$ of bubble and/or irregularly shaped void surface area per hour.

Preferably, the kinetic energy dissipation rate in the high shear mixing zone is in the range of from 0.5 to 25 kW/m$^3$, relative to the total volume of suspension present in the system, more preferably from 0.5 to 10 kW/m³, most preferably from 0.5 to 5 kW/m³, and in particular, from 0.5 to 2.5 kW/m³.

The high shear mixing zone(s) may be part of the system inside or outside the reactor vessel. Preferably, the high shear mixing zone(s) project through the walls of the reactor vessel such that the high shear mixing zone(s) discharges its contents into the reactor vessel. Suitably, the system comprises a plurality of high shear mixing zones, preferably up to 250 high shear mixing zones, more preferably less than 100, most preferably less than 50, for example 10 to 50 high shear mixing zones. The plurality of high shear mixing zones may discharge their contents into or may be located within a single reactor vessel which has an advantage of significantly reducing the size of a commercial Fischer-Tropsch plant. It is envisaged that a plurality of the reactor vessels may be connected in series, preferably, 2 to 4, for example, 2 or 3, in which case the high shear mixing zones are divided between the reactor vessels. Preferably, the plurality of high shear mixing zones may be spaced uniformly inside or outside the reactor vessel(s), for example, the high shear mixing zones may be spaced uniformly at or near the top of the reactor vessel(s).

Suitably, the reactor vessel has a diameter of from 5 to 15 metres, preferably 7.5 to 10 metres, more preferably 7.5 to 8 metres. Suitably, the reactor vessel has a length of from 5 to 30 metres, preferably 10 to 20 metres, for example 15 to 20 metres.

The reactor vessel may be arranged such that its longitudinal axis is substantially vertical in which case the high shear mixing zone(s) may discharge the mixture of synthesis gas and suspension in a downwards direction (down-shot) or in an upwards direction into the reactor vessel(s) (up-shot). The high shear mixing zone(s) may also discharge into the reactor vessel (either upwardly or downwardly) at an angle relative to the longitudinal axis of the reactor vessel.

It is also envisaged that the reactor vessel may be arranged such that the longitudinal axis of the reactor vessel is substantially horizontal in which case the high shear mixing zone(s) may discharge the mixture of synthesis gas and suspension in a direction along the longitudinal axis of the reactor vessel or a series of high shear mixing zone(s) may be arranged along the reactor vessel and discharge their contents radially inwardly into the reactor vessel.

Suitably, the high shear mixing zone(s) may be angled, preferably at an angle of less than 30°, more preferably at an angle of less than 20°, for example less than 10° relative to the longitudinal axis of the reactor vessel.

The volume of suspension present in the high shear mixing zone(s) is substantially smaller than the volume of suspension present in the remainder of the reactor system. Suitably, the volume of suspension present in the high shear mixing zone(s) is less than 20%, preferably less than 10% of the volume of suspension present in the remainder of the reactor system.

The high shear mixing zone(s) may comprise any device suitable for intensive mixing or dispersing of a gaseous stream in a suspension of solids in a liquid medium, for example, a rotor-stator device, or an injector-mixing nozzle. Suitably, the high shear mixing zone(s) break down the synthesis gas into gas bubbles and/or irregularly shaped gas voids and disperses said bubbles and/or gas voids in the suspension.

The injector-mixing nozzle(s) can advantageously be executed as a venturi tube (c.f. "Chemical Engineers' Handbook" by J. H. Perry, $3^{rd}$ edition (1953), p.1285, FIG. 61), preferably an injector mixer (c.f. "Chemical Engineers' Handbook" by J H Perry, $3^{rd}$ edition (1953), p 1203, FIG. 2 and "Chemical Engineers' Handbook" by R H Perry and C H Chilton $5^{th}$ edition (1973) p 6–15, FIGS. 6–31) or most preferably as a liquid-jet ejector (c.f. "Unit Operations" by G G Brown et al, $4^{th}$ edition (1953), p.194, FIG. 210). The injector-mixing nozzle(s) may also be executed as a venturi plate or a high shear pumping means positioned within a conduit wherein the conduit has an inlet for the suspension and an outlet for the mixture of suspension and synthesis gas. Alternatively, the injector-mixing nozzle(s) may be executed as a "gas blast" or "gas assist" nozzle where gas expansion is used to drive the nozzle (c.f. "Atomisation and Sprays" by Arthur H Lefebvre, Hemisphere Publishing Corporation, 1989). Where the injector-mixing nozzle(s) is executed as a "gas blast" or "gas assist" nozzle, the suspension is fed to the nozzle at a sufficiently high pressure to allow the suspension to pass through the nozzle while the synthesis gas is fed to the nozzle at a sufficiently high pressure to achieve high shear mixing within the nozzle.

Where the injector mixing nozzle(s) is executed as a venturi plate located within a conduit, the venturi plate is preferably located close to the outlet of the conduit, for example, within 1 metre, preferably within 0.5 metres of the outlet. Suspension is introduced into the conduit through the inlet at a sufficiently high pressure for the suspension to pass through apertures in the venturi plate while synthesis gas is drawn into the conduit through at least one opening(s), preferably 2 to 5 openings, in the walls of the conduit. Preferably, the opening(s) is located in the walls of the conduit downstream of the venturi plate, more preferably, immediately downstream of the venturi plate, for example, within 1 metre, preferably within 0.5 metres of the venturi plate. Suspension having gas bubbles and/or irregularly shaped gas voids (hereinafter "gas voids") dispersed therein is discharged into the reactor vessel though the outlet of the conduit.

Where the injector mixing nozzle(s) is executed as a high shear pumping means located within a conduit, the high shear pumping means is preferably a paddle or propeller having high shear blades. Suitably, the high shear pumping means is located close to the outlet of the conduit, for example, within 1 metre, preferably, within 0.5 metres of the outlet. Synthesis gas is injected into the conduit, for example, via a sparger, located either immediately upstream or immediately downstream of the high shear pumping means, for example, within 1 metre, preferably within 0.5 metres of the high shear pumping means. Preferably, the synthesis gas is injected into the conduit immediately upstream of the high shear pumping means. Without wishing to be bound by any theory, the injected synthesis gas is broken down into gas bubbles and/or gas voids by the fluid shear imparted to the suspension by the high shear pumping means. The resulting suspension containing entrained gas bubbles and/or gas voids is then discharged into the reactor vessel through the outlet of the conduit.

Where the injector mixing nozzle(s) is executed as a venturi nozzle(s) (either a as a venturi tube or as a venturi plate), the pressure drop of the suspension over the venturi nozzle(s) is typically in the range of from 1 to 40 bar, preferably 2 to 15 bar, more preferably 3 to 7 bar, most preferably 3 to 4 bar. Preferably, the ratio of the volume of gas ($Q_g$) to the volume of liquid ($Q_l$) passing through the venturi nozzle(s) is in the range 0.5:1 to 10:1, more preferably 1:1 to 5:1, most preferably 1:1 to 2.5:1, for example, 1:1 to 1.5:1 (where the ratio of the volume of gas ($Q_g$) to the volume of liquid ($Q_l$) is determined at the desired reaction temperature and pressure).

Where the injector mixing nozzle(s) is executed as a gas blast or gas assist nozzle(s), the pressure drop of gas over the nozzle(s) is preferably in the range 3 to 100 bar and the pressure drop of suspension over the nozzle(s) is preferably in the range of from 1 to 40 bar, preferably 4 to 15 bar, most preferably 4 to 7 bar. Preferably, the ratio of the volume of gas ($Q_g$) to the volume of liquid ($Q_l$) passing through the gas blast or gas assist nozzle(s) is in the range 0.5:1 to 50:1, preferably 1:1 to 10:1 (where the ratio of the volume of gas ($Q_g$) to the volume of liquid ($Q_l$) is determined at the desired reaction temperature and pressure).

Suitably, the shearing forces exerted on the suspension in the high shear mixing zone(s) are sufficiently high that at least a portion of the synthesis gas is broken down into gas bubbles having diameters in the range of from 1 $\mu$m to 10 mm, preferably from 30 $\mu$m to 3000 $\mu$m, more preferably from 30 $\mu$m to 300 $\mu$m.

Without wishing to be bound by any theory, it is believed that any irregularly shaped gas voids are transient in that they are coalescing and fragmenting on a rapid time scale, for example, over a period of up to 500 ms. The gas voids have a wide size distribution with smaller gas voids having an average diameter of 1 to 2 mm and larger gas voids having an average diameter of 10 to 15 mm.

Suspension may be withdrawn from the reactor vessel and may be recycled to the reactor vessel after passing through the high shear mixing zone(s). The suspension which is recycled to the high shear mixing zone(s) (hereinafter referred to as "suspension recycle stream") may be cooled outside of the high shear mixing zone(s) and the reactor vessel, in order to assist in the removal of exothermic heat of reaction from the system, for example, by passing the suspension recycle stream through an external heat exchanger. Preferably, the suspension recycle stream is cooled to a temperature of 1 to 30° C. below, preferably not more than 12° C. below the temperature of the suspension in the reactor vessel. Alternatively, cooling may be provided within the reactor vessel by means of an internal heat exchanger, for example, heat transfer tubes, coils or plates, positioned within the suspension in the reactor vessel. It is also envisaged that the suspension may be cooled by means of both an external and an internal heat exchanger.

A gaseous phase comprising unconverted synthesis gas may be separated from the suspension either within the reactor vessel and/or in an external gas separation zone. The separated gaseous phase may then be recycled to the high shear mixing zone(s). This gaseous recycle stream may comprise carbon dioxide, inert gases such as nitrogen, vaporized low boiling liquid hydrocarbons, vaporized water by-product and gaseous hydrocarbons having, for example, from 1 to 3 carbon atoms such as methane, ethane and propane, in addition to unconverted synthesis gas.

The gaseous recycle stream may be cooled before being recycled to the high shear mixing zone(s), for example, by passing the gaseous recycle stream through a heat exchanger, to assist in the removal of the exothermic heat of reaction from the system. Where the gaseous recycle stream is cooled to below its dew point, any vaporized low boiling liquid hydrocarbons and any vaporized water by-product will condense out of the gaseous recycle stream and these condensed liquids are preferably removed from the system using a suitable separation means, for example, the heat exchanger may be fitted with a liquid trap. Water by-product may then be separated from the condensed low boiling liquid hydrocarbon products using a suitable separation means, such as a decanter. The low boiling hydrocarbon products may then be recycled to the high shear mixing zone(s) and/or the reactor vessel. Fresh synthesis gas may be fed to the gaseous recycle stream, either upstream or downstream of the heat exchanger. Where the fresh synthesis gas has not been pre-cooled, it is preferred that the fresh synthesis gas is fed to the gaseous recycle stream upstream of the heat exchanger. Preferably, the gaseous stream which is recycled to the high shear mixing zone comprises from 5 to 50% by volume of fresh synthesis gas.

Preferably, a purge stream is taken from the gaseous recycle stream to prevent accumulation of gaseous by-products, for example, methane, or any inert gases, for example, nitrogen in the system. If desired, any gaseous intermediate products (gaseous hydrocarbons, for example, having 2 or 3 carbon atoms) may be separated from the purge stream. Such gaseous intermediate products may recycled to the system where they may be converted to liquid hydrocarbon products.

The purge stream may passed to a power generator where combustion of the unconverted synthesis gas, gaseous hydrocarbons and any vaporized low boiling liquid hydrocarbons is used to generate electricity. At least a portion of said electricity may be used in the operation of the reactor system used in the process of the present invention.

The power generator usually comprises one or more prime movers. Suitably, the prime mover may be a gas turbine, a steam turbine or a reciprocating internal combustion engine or a combination thereof. Preferably the prime mover is a gas turbine and is usually driven by steam produced from the heat generated upon combustion of the purge stream.

The electricity generated from the purge stream may be used, for example, to operate the ancillary equipment of the reactor system, for example, compressors, slurry pumps, or heat exchangers.

As discussed below, the synthesis gas used in the process of the present invention is preferably derived from a natural gas stream. It is envisaged that a first portion of a natural gas stream may be used to produce synthesis gas and a second portion of the natural gas stream may be passed to a liquefaction unit to produce liquefied natural gas. Preferably at least a portion of the electricity generated from the purge stream may be used in the operation of the liquefaction unit e.g. to power the refrigeration compressors.

Preferably, a stream comprising a vaporizable low boiling hydrocarbon(s) (for example pentanes, hexanes or hexenes) may be introduced into the high shear mixing zone(s) and/or the reactor vessel and/or into the suspension recycle stream. Without wishing to be bound by any theory, it is believed that vaporisation of the low boiling hydrocarbon(s) (hereinafter referred to as "low boiling solvent") in the high shear mixing zone(s) and/or the reactor vessel aids and enhances the mixing of the synthesis gas, liquid medium and the solid particulate Fischer-Tropsch catalyst thereby increasing conversion of the synthesis gas to liquid hydrocarbon products. Moreover, vaporisation of the low boiling solvent will also assist in removing some of the exothermic heat of reaction thereby allowing more control over the product selectivities and minimising the production of gaseous by-products, for example, methane. For avoidance of doubt, it is envisaged that the low boiling solvent may vaporise in both the reactor vessel and the high shear mixing zone(s). The gaseous recycle stream and purge stream may therefore comprise vaporized low boiling solvent in addition to vaporized low boiling liquid hydrocarbons, vaporized water by-product, unconverted synthesis gas and gaseous hydrocarbons having from 1 to 3 carbon atoms. As discussed above, the gaseous recycle stream may be cooled before being recycled to the high shear mixing zone(s). Any vaporized low boiling solvent may condense, together with any vaporized low boiling liquid hydrocarbon products and any vaporized water by-product, upon cooling the gaseous recycle stream to below its dew point. Preferably, the condensed liquids are removed from the system, as described above, and water by-product may then be separated from the condensed liquids using a suitable separation means, also as described above. The remaining condensed liquids may then be recycled to the high shear mixing zone(s) and/or the reactor vessel and/or to the suspension recycle stream.

For practical reasons the reactor vessel may not be totally filled with suspension during the process of the present invention so that above a certain level of suspension a gas cap comprising unconverted synthesis gas, methane, carbon dioxide, inert gases, gaseous hydrocarbon products vaporized low boiling liquid hydrocarbon products and any vaporized low boiling solvent is present in the top of reactor vessel. Suitably, the volume of the gas cap is not more than 40%, preferably not more than 30% of the volume of the reactor vessel. The high shear mixing zone(s) may discharge into the reactor vessel either above or below the level of suspension in the reactor vessel or may be totally submerged below the level of the suspension. An advantage of the high shear mixing zone(s) discharging below the level of suspension is that this improves the contact between the synthesis gas and the suspension in the reactor vessel. It is envisaged that the high shear mixing zone(s), for example, the venturi nozzle(s), may be located entirely below the level of the suspension in the reactor vessel, in which, the synthesis gas is fed to the high shear mixing zone(s) via a gas line which passes through the walls of the reactor vessel and communicates with an inlet of the high shear mixing zone(s).

Where the reactor vessel has a gas cap, the gaseous recycle stream may be withdrawn from the gas cap. It is also envisaged that the reactor vessel may be fitted with an overhead condenser or cooler for removal of heat from the gases in the gas cap. Where the reactor vessel is fitted with an overhead condenser or cooler, the gaseous recycle stream may be withdrawn from the overhead condenser or cooler (i.e. is withdrawn indirectly from the reactor vessel). Any low boiling liquid hydrocarbon products and low boiling solvent which condense in the condenser or cooler may be collected and recycled to the high shear mixing zone(s), the reactor vessel or the suspension recycle stream (after having separated any water by-product).

In a preferred embodiment the process is carried out using at least one injector-mixing nozzle. It has been found that intensive mixing of the synthesis gas, the liquid medium and the solid particulate Fischer-Tropsch catalyst can be achieved in the injector-mixing nozzle(s) leading to high conversions of synthesis gas to liquid hydrocarbon products in the reactor vessel. The injector-mixing nozzle(s) may draw in the synthesis gas through at least one opening in its side wall (a venturi nozzle). Alternatively, as described above, the synthesis gas may be supplied at high pressure to the injector-mixing nozzle(s) through at least one opening in its side wall (a "gas blast" or "gas assist" nozzle). An advantage of using a "gas blast" or "gas assist" nozzle as the high shear mixing zone(s) is that there is a reduced duty on the slurry pump.

More than one injector-mixing nozzle, preferably up to 150, more preferably less than 100, most preferably less than 50, for example 10 to 50 injector-mixing nozzles may discharge into a single reactor vessel.

Although the injector-mixing nozzle(s) can be placed at any position on the walls of the vessel (for example, on the top, bottom or side walls), very good mixing can be achieved when the injector-mixing nozzle(s) is situated at or near the top of the reactor vessel and the suspension is removed from the reactor vessel at or near its bottom. Therefore the reactor vessel is preferably provided at or near its top with at least one injector-mixing nozzle and the suspension recycle stream is preferably withdrawn from at or near the bottom of the reactor vessel. Preferably, the suspension recycle stream is at least in part recycled via an external conduit (slurry recycle line) to the top of the injector-mixing nozzle(s) through which it is injected into the top of the reactor vessel, synthesis gas being introduced through one or more openings in the side wall of the injector-mixing nozzle(s). Suitably, a mechanical pumping means, for example, a slurry pump is located in the external conduit. Suitably, the power input of the slurry pump is equivalent to an energy dissipation rate of at least 0.5 kW/m$^3$, preferably 0.5 to 25 kW/m$^3$, more preferably 0.5 to 10 kW/m$^3$, most preferably, 0.5 to 2.5 kW/m$^3$ based on the total volume of slurry in the system. Preferably, an external heat-exchanger is positioned on the external conduit to remove the heat of reaction. Preferably the external heat exchanger is located downstream of the mechanical pumping means. The reactor vessel may also be provided with an internal heat exchanger positioned below the level of the suspension in the reactor vessel. It is also envisaged that the exothermic heat of reaction may be removed from the system entirely by means of the internal heat exchanger.

Preferably, the ratio of the volume of the external conduit to the volume of the reactor vessel (excluding the volume of any external heat exchanger) is in the range of 0.005:1 to 0.2:1.

Preferably, up to 50% by volume, more preferably up to 20% by volume of the hydrogen component of the synthesis gas (hereinafter "hydrogen component") is introduced into the suspension recycle stream, for example, into the external conduit.

Without wishing to be bound by any theory, it is believed that the unconverted synthesis gas which is present in the suspension recycle stream may be depleted in hydrogen. An advantage of injecting the hydrogen component into the suspension recycle stream is that this will maintain the ratio of hydrogen to carbon monoxide in the synthesis gas at an optimum value thereby improving the conversion of synthesis gas to higher hydrocarbons. A further advantage of injecting the hydrogen component into the suspension recycle stream is that this may also stabilize the catalyst.

It is also envisaged that up to 50% by volume, preferably up to 20% by volume of the carbon monoxide component of the synthesis gas (hereinafter "carbon monoxide component") may be introduced into the suspension recycle stream.

Suitably, the hydrogen component and/or the carbon monoxide component is introduced into the external conduit either upstream or downstream of the mechanical pumping means, preferably downstream of the mechanical pumping means. Preferably, the hydrogen component and/or carbon monoxide component is introduced to the external conduit upstream of the external heat exchanger. The hydrogen component and/or the carbon monoxide component may be introduced into the external conduit at more than one position along the length of the external conduit.

Preferably, the hydrogen component and/or the carbon monoxide component is introduced into the external conduit via a gas nozzle. Preferably, the pressure drop over the gas nozzle is at least 0.1 bar, more preferably, at least 0.5 bar, for example, at least 1 bar.

Where necessary, the ratio of hydrogen to carbon monoxide in the unconverted synthesis gas within the reactor vessel may be adjusted by feeding additional hydrogen and/or carbon monoxide directly into the reactor vessel, for example, via a gas sparger.

Where the hydrogen component is introduced into the suspension recycle stream in the substantial absence of carbon monoxide, the hydrogen may be obtained from synthesis gas, for example, the hydrogen may be separated from synthesis gas by pressure swing adsorption or by diffusion through a membrane system.

As discussed above, the system may comprise a plurality of reactor vessels connected in series, preferably 2 to 4, for example 2 or 3 reactor vessels. Where 2 reactor vessels are connected in series, a suspension recycle stream may be returned to the same reactor vessel after having been passed through the injector-mixing nozzle(s) while a gaseous stream comprising unconverted synthesis gas may be withdrawn from the first reactor vessel and may be recycled to the second reactor vessel in the series via at least one injector-mixing nozzle. This arrangement improves the conversion of synthesis gas to liquid hydrocarbon products. Alternatively, it may be advantageous to withdraw the suspension from the first reactor vessel and to discharge the suspension into the second reactor vessel after having passed the suspension through the high shear mixing zone(s). The suspension from the second reactor in the series may then be recycled back to the first reactor in the series via the high shear mixing zone(s).

Where the reactor vessel has a gas cap, advantageously the gaseous recycle stream is withdrawn from the gas cap, through the walls of the reactor vessel, and is recycled to the injector-mixing nozzle(s). It is also envisaged that where the injector mixing nozzle(s) is at least partially located above the level of suspension in the reactor vessel that the gaseous recycle stream may be recycled directly from the gas cap to the injector-mixing nozzle(s). An advantage of withdrawing the synthesis gas from the gas cap through the walls of the reactor vessel, is that in this manner the temperature of the suspension in the vessel can be advantageously controlled by cooling the gaseous recycle stream in a heat exchanger located outside the reactor vessel. This temperature control can be further improved if fresh synthesis gas is added to the gaseous recycle stream before it is cooled (upstream of the heat exchanger) or is pre-cooled. Preferably, the ratio of hydrogen to carbon monoxide of the synthesis gas used in the process of the present invention is in the range of from 20:1 to 0.1:1 by volume, especially 5:1 to 1:1 by volume, typically 2:1 by volume. Additional components such as methane, carbon dioxide, nitrogen and water may be present in the synthesis gas.

The synthesis gas may be prepared using any of the processes known in the art including partial oxidation of hydrocarbons, steam reforming, gas heated reforming, microchannel reforming (as described in, for example, U.S. Pat. No. 6,284,217 which is herein incorporated by reference), plasma reforming, autothermal reforming and any combination thereof. A discussion of a number of these synthesis gas production technologies is provided in "Hydrocarbon Processing" V78, N.4, 87–90, 92–93 (April 1999) and "Petrole et Techniques", N. 415, 86–93 (July-August 1998). It is also envisaged that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187–196. Alternatively, the synthesis gas may be obtained by short contact time catalytic partial oxidation of hydrocarbonaceous feedstocks as described in EP 0303438. Preferably, the synthesis gas is obtained via a "Compact Reformer" process as described in "Hydrocarbon Engineering", 2000, 5, (5), 67–69; "Hydrocarbon Processing", 79/9, 34 (September 2000); "Today's Refinery", 15/8, 9 (August 2000); WO 99/02254; and WO 200023689. An advantage of the process of the present invention is that where the synthesis gas is obtained via a "Compact Reformer" process, the synthesis gas is generally at a pressure of above 20 bar. Accordingly, there is no requirement to lower the pressure of the synthesis gas before feeding the syngas to the injector-mixing nozzle(s) thereby providing an energy efficient integrated Reforming/Fischer Tropsch process. In particular, the pressure of synthesis gas obtained via a "Compact Reformer" process is generally sufficiently high to achieve high shear mixing within a "gas blast" or "gas assist" nozzle. Preferably, the synthesis gas is derived from natural gas.

Preferably, the hydrocarbons produced using the process of the present invention (hereinafter "hydrocarbon products") comprise a mixture of hydrocarbons having a chain length of greater than 2 carbon atoms, typically greater than 5 carbon atoms. Suitably, the hydrocarbon products comprise a mixture of hydrocarbons having chain lengths of from 5 to about 90 carbon atoms. Preferably, a major amount, for example, greater than 60% by weight, of the hydrocarbon products have chain lengths of from 5 to 30 carbon atoms.

Suitably, the liquid medium comprises one or more of the hydrocarbon products which are liquid under the conditions of elevated temperature and pressure. This has an advantage that there is no requirement to separate the liquid medium from the hydrocarbon products.

The solid particulate catalyst which may be employed in the process of the present invention is any catalyst known to be active in Fischer-Tropsch synthesis. For example, Group VIII metals whether supported or unsupported are known Fischer-Tropsch catalysts. Of these iron, cobalt and ruthenium are preferred, particularly iron and cobalt, most particularly cobalt.

A preferred catalyst is supported on a support such as an elemental carbon support, for example, graphite or an inorganic oxide, preferably a refractory inorganic oxide support. Preferred supports include silica, alumina, silica-alumina, the Group IVB oxides, titania (primarily in the rutile form) and zinc oxide. The supports generally have a surface area of less than about 100 $m^2/g$, preferably less than 50 $m^2/g$, more preferably less than 25 $m^2/g$, for example, about 5 $m^2/g$.

The catalytic metal is present in catalytically active amounts usually about 1–100 wt %, the upper limit being attained in the case of iron based catalysts, preferably 2–40 wt %. Promoters may be added to the catalyst and are well known in the Fischer-Trospch catalyst art. Promoters can include ruthenium, platinum or palladium (when not the primary catalyst metal), rhenium, hafnium, cerium, lanthanum, aluminium and zirconium, and are usually present in amounts less than the primary catalytic metal (except for ruthenium which may be present in coequal amounts), but the promoter:metal ratio should be at least 1:10. Preferred promoters are rhenium and hafnium.

A preferred catalyst is cobalt supported on an inorganic oxide, preferably zinc oxide.

Preferably, the solid particulate Fischer-Tropsch catalyst has a particle size of from 5 to 500 microns, preferably 5 to 100 microns, for example, in the range 5 to 30 microns.

Preferably, the suspension of catalyst discharged into the reactor vessel comprises less than 40% wt of catalyst particles, more preferably 10 to 30% wt of catalyst particles, most preferably 10 to 20% wt of catalyst particles.

It is also envisaged that inert particles may be added to the suspension of the solid particulate Fischer-Tropsch catalyst in the liquid medium. Without wishing to be bound by any theory it is believed that these inert particles may improve the dispersion of the solid particulate Fischer-Tropsch catalyst in the liquid medium, absorb at least a portion of the exothermic heat of reaction by acting as a heat sink, enhance the mixing of the suspension and the synthesis gas by reducing the cohesive forces between the catalyst particles, modify the density of the slurry, or control foaming.

Suitably the inert particles are stable in the suspension under the conditions within the reactor system. Preferably, the inert particles may be formed from a material selected from the group consisting of inorganic materials, ceramics, polymers, carbon, metals and alloys. Typical examples of ceramic materials include silica, alumina, zirconia, titania, zinc oxide, and glass. Suitable polymers may be selected from e.g. polyethylene, polypropylene and polystyrene. Suitable metals and alloys include, e.g., aluminium alloys and stainless steel. Preferably the inert particles may be formed from a material used as the support for the Fischer-Tropsch catalyst. Alternatively, the inert particles may comprise spent or deactivated catalyst particles in particular spent or deactivated particulate Fischer-Tropsch catalyst.

The inert particles generally have a surface area of less than about 100 $m^2/g$, preferably less than 40 $m^2/g$, more preferably less than 10 $m^2/g$, for example, about 2 $m^2/g$.

Preferably, the inert particles have an average particle size in the range 0.05 microns to 5 millimeters, usually 1 to 1000 microns and especially 5 to 500 microns e.g. 10–200 microns. The particulate Fischer-Tropsch catalyst and the inert particle(s) may have a different average particle size such that the suspension has a bimodal particle size distribution. Alternatively the particulate Fischer-Tropsch catalyst and the inert particle(s) may be of substantially the same average particle size providing the suspension with a unimodal particle size distribution. When more than one type of inert particle is employed, the particulate Fischer-Tropsch catalyst and the differing inert particles may advantageously have different average particle sizes (multimodal particle size distribution).

Preferably, the weight ratio of the solid particulate Fischer-Tropsch catalyst to the inert particles is in the range of 100:1 to 1:100, preferably 20:1 to 1:2, advantageously 10:1 to 1:1 and especially 5:1 to 2:1.

The process of the present invention is preferably carried out at a temperature of 180–380° C., more preferably 180–280° C., most preferably 190–240° C.

The process of the invention is preferably carried out at a pressure of 5–50 bar, more preferably 15–35 bar, generally 20–30 bar.

The process of the present invention can be operated in batch or continuous mode, the latter being preferred.

In a continuous process, in order to achieve a sufficiently high productivity, the liquid component of the suspension should be present in the reactor vessel for a certain period of time. It has been found that the average residence time of the liquid phase (i.e. the liquid component of the suspension) in the reactor vessel is advantageously in the range from 10 minutes to 50 hours, preferably, 1 to 30 hours.

Suitably, the gas residence time in the high shear mixing zone(s) (for example, the injector-mixing nozzle(s)) is in the range 20 milliseconds to 2 seconds, preferably 50 to 250 milliseconds.

Suitably, the gas residence time in the reactor vessel is in the range 10 to 240 seconds, preferably 20 to 90 seconds.

Suitably, the gas residence time in the external conduit is in the range 10 to 180 seconds, preferably 25 to 60 seconds.

Suitably, the process of the present invention is operated with a gas hourly space velocity (GHSV) in the range 100 to 40000 $h^{-1}$, more preferably 1000 to 30000 $h^{-1}$, most preferably 2000 to 15000, for example 4000 to 10000 $h^{-1}$ at normal temperature and pressure (NTP) based on the feed volume of synthesis gas at NTP.

In a continuous process, part of the suspension is continuously removed from the system and is passed to a suitable liquid-solid separation means, where at least a portion of the liquid medium and liquid hydrocarbons are separated from the catalyst. A gas separation means may be positioned upstream of the liquid-solid separation means to remove any entrained gases, for example, the external heat exchanger positioned on the external conduit may incorporate a gas separation means. Entrained gases may also be separated from the suspension in the liquid-solid separation means. Examples of suitable liquid-solid separation means include hydrocyclones, filters, gravity separators and magnetic separators. Alternatively, liquid medium and liquid hydrocarbons may be separated from the catalyst by evaporation. The separated liquids are then passed to a product purification stage where water by-product and liquid medium are removed from the liquid hydrocarbons. As discussed above, the purification stage may be simplified by using one or more of the hydrocarbon products (which are liquid under the condition of elevated temperature and pressure) as the liquid medium in which case there is no requirement to separate the liquid medium from the hydrocarbon products. The catalyst may be recycled as a concentrated slurry to the reactor vessel. Fresh activated catalyst may be added either to the recycled slurry or directly into the reactor vessel.

In order to prevent the accumulation of water by-product in the system it is preferred that at least a portion of the water by-product is removed from the suspension recycle stream. This may be achieved by taking a side stream from the suspension recycle stream downstream of the heat exchanger. The liquid components of the side stream are separated from the catalyst (as described above) and water by-product is removed from the separated liquids (also as described above) before recycling the remaining separated liquid components back to the high shear mixing zone. The separated catalyst may be recycled to the reactor vessel as a concentrated slurry (as described above).

It is envisaged that removal of water by-product from the system can be incorporated into the product separation stage, by recycling a portion of the separated liquids, from which water has been removed, back to the high shear mixing zone.

The hydrocarbon products from the purification stage may be fed to a hydrocracking stage, for example, a catalytic hydrocracking stage which employs a catalyst comprising a metal selected from the group consisting of cobalt, molybdenum, nickel and tungsten supported on a support material such as alumina, silica-alumina or a zeolite. Preferably, the catalyst comprises cobalt/molybdenum or nickel/molybdenum supported on alumina or silica-alumina. Suitable hydrocracking catalysts include catalysts supplied by Akzo Nobel, Criterion, Chevron, or UOP.

BRIEF DESCRIPTION OF THE DRAWING

The invention will now be illustrated with reference to the attached FIGURE which is a schematic of the process of the invention.

DETAILED DESCRIPTION OF PREFERRED EMBODIMENTS

Figure 1:
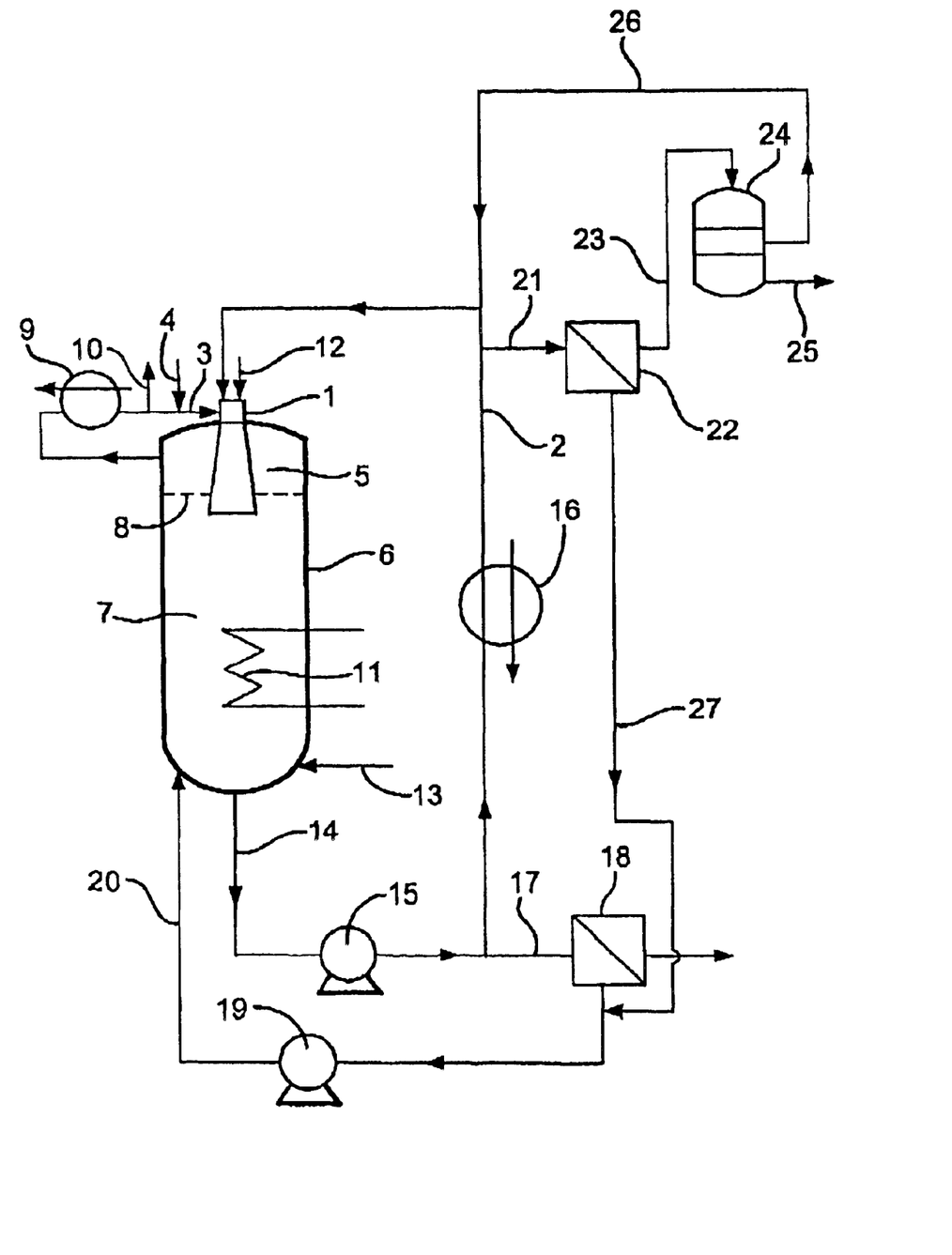

A suspension of a catalyst in a liquid medium is recycled to an injector-mixing nozzle (1) via a line (2). Through one or more openings in the side wall of the injector-mixing nozzle (1) the suspension draws in synthesis gas, which is introduced into the injector-mixing nozzle (1) via a line (3). Fresh synthesis gas is introduced via a line (4) into the line (3) through which unconverted synthesis gas is recycled from a gas cap (5) which is present in the upper part of a vessel (6), the lower part of which contains a suspension (7) of the catalyst in a mixture of the liquid medium and liquid hydrocarbon products. A dotted line (8) in the FIGURE denotes the upper level of the suspension (7) in the vessel (6).

By means of cooling in a heat exchanger (9) the gaseous recycle stream passing through the line (3) is maintained at the correct operating temperature. Suitably, the heat exchanger (9) is a condenser having a water trap for removing water by-product from the system.

A purge stream (10) is taken from the line (3) to prevent the build up of gaseous by-products or inert gas in the gas cap (5). Optionally, a heat exchanger (11) e.g. cooling tubes is provided below the level of the suspension (7) in the vessel (6) to assist in removing the exothermic heat of reaction.

Optionally, a stream of low boiling hydrocarbon liquid(s) (low boiling solvent) may-be introduced to the injector-mixing nozzle (1) via line (12) or alternatively to the vessel (6), via line (13). Where low boiling solvent is introduced to the system this may condense in the heat exchanger (9). The condensed low boiling solvent may be separated from the condensed water by-product in a decanter (not shown). The separated low boiling solvent may then be recycled to the system.

Via a lower outlet opening of the injector-mixing nozzle (1) a mixture of catalyst, liquid medium, liquid hydrocarbon products and unconverted synthesis gas pass into the vessel (6) below the level (8) of the suspension (7). The unconverted synthesis gas then separates into the gas cap (5).

Via a line (14) the suspension (7) is withdrawn from the bottom of the vessel (6) and at least a portion of the suspension is recycled to the injector-mixing nozzle (1) by means of mechanical pump (15) and the line (2). The power of the pump is equivalent to an energy dissipation rate of at least 0.5 kW/m³ based on the total volume of suspension in the system. By means of cooling in a heat exchanger (16) the recycled suspension in the line (2) is maintained at the correct operating temperature.

Via a line (17) a portion of the suspension (7) is withdrawn from the system. By a suitable separation means (18), e.g. a hydrocyclone, filter, gravity separator or magnetic separator, or alternatively, by distillation, the liquid medium and liquid hydrocarbon products may be separated from the suspended catalyst. Separated catalyst may be returned to the vessel (6) as a slurry via a slurry pump (19) and a line (20). The separated liquid medium and liquid hydrocarbon products may be passed from the separation means (18) to a purification zone (not shown).

A portion of suspension may be withdrawn from line (2) and may be passed along line (21) to a separation means (22) where the liquid components of the suspension are separated from the catalyst (e.g., as described above). The separated liquids are then passed along line (23) to a decanter (24) where water by-product is removed from the system via line (25). The remaining liquids are then reintroduced into line (2) via line (26). The separated catalyst, from decanter (24), is introduced as a slurry into line (20) via a line (27).

What is claimed is:

1. A process for the conversion of synthesis gas to hydrocarbons comprising contacting the synthesis gas at an elevated temperature and pressure with a suspension comprising a solid particulate catalyst suspended in a liquid medium, which contacting takes place in a system comprising at least one high shear mixing zone and a reactor vessel wherein the volume of suspension present in the high shear mixing zone(s) is substantially less than the volume of suspension present in the reactor vessel, mixing the suspension with synthesis gas in the high shear mixing zone(s), discharging the resulting mixture of suspension and synthesis gas from the high shear mixing zone(s) into the reactor vessels, wherein kinetic energy is dissipated to the suspension present in the high shear mixing zone(s) at a rate of at least 0.5 kW/m³ relative to the total volume of suspension present in the system.

2. A process as claimed in claim 1 wherein the kinetic energy dissipation rate in the high shear mixing zone is in the range of from 0.5 to 10 kW/m³.

3. A process as claimed in claim 1 wherein the synthesis gas is dispersed in the suspension in the high shear mixing zone(s) in the form of gas bubbles and/or irregularly shaped gas voids.

4. A process as claimed in claim 1 wherein the volumetric mass transfer rate is in the range 2 to 10,000, kg-moles/h of carbon monoxide transferred per m³ of suspension.

5. A process as claimed in claim 3 wherein the mass transfer rate is in the range $5 \times 10^{-3}$ to $5 \times 10^{-6}$ kg-moles carbon monoxide transferred per m² of bubble and/or irregularly shaped void surface area per hour.

6. A process as claimed in claim 1 wherein the process is continuous.

7. A process as claimed in claim 6 wherein the average residence time of the liquid component of the suspension in the reactor vessel is in the range from 10 minutes to 50 hours.

8. A process as claimed in claim 6 wherein the gas hourly space velocity (GHSV) is in the range 100 to 40000 h⁻¹, at normal temperature and pressure (NTP) based on the feed volume of synthesis gas at NTP.

9. A process as claimed in claim 1 wherein the high shear mixing zone(s) projects through the walls of the reactor vessel or is located within the reactor vessel.

10. A process as claimed in claim 9 wherein the system comprises up to 250 high shear mixing zones, which project through the walls of a single reactor vessel or are located within a single reactor vessel.

11. A process as claimed in claim 1 wherein 2 to 4 reactor vessels are connected in series.

12. A process as claimed in claim 1 wherein the reactor vessel is arranged such that its longitudinal axis is substantially vertical and wherein the high shear mixing zone(s) discharge the mixture of synthesis gas and suspension in a downwards direction (down-shot) or in an upwards direction (upshot) into the reactor vessel(s).

13. A process as claimed in claim 1 wherein the reactor vessel is arranged such that its longitudinal axis is substantially horizontal and wherein the high shear mixing zone(s) discharge the mixture of synthesis gas and suspension in a direction along the longitudinal axis or radially inwardly into the reactor vessel.

14. A process as claimed in claim 12 wherein the high shear mixing zone(s) are angled at an angle of less than 30°, relative to the longitudinal axis of the reactor vessel.

15. A process as claimed in claim 1 wherein the volume of suspension present in the high shear mixing zone(s) is less than 20%, of the volume of suspension present in the remainder of the reactor system.

16. A process as claimed in claim 1 wherein the high shear mixing zone(s) comprises an injector-mixing nozzle(s).

17. A process as claimed in claim 16 where the injector-mixing nozzle(s) is a venturi nozzle(s).

18. A process as claimed in claim 17 wherein the pressure drop of the suspension over the venturi nozzle(s) is in the range of from 1 to 40 bar and wherein the ratio of the volume of gas ($Q_g$) to the volume of liquid ($Q_l$) passing through the venturi nozzle(s) is in the range 0.5:1 to 10:1, (where the ratio of the volume of gas ($Q_g$) to the volume of liquid ($Q_l$) is determined at the desired reaction temperature and pressure).

19. A process as claimed in claim 16 wherein the injector-mixing nozzle(s) is a gas blast nozzle(s).

20. A process as claimed in claim 19 wherein the pressure drop of gas over the nozzle(s) is in the range 3 to 100 bar, the pressure drop of suspension over the nozzle(s) is in the range of from 1 to 40 bar, and the ratio of the volume of gas ($Q_g$) to the volume of liquid ($Q_l$) passing through the gas blast nozzle(s) is in the range 0.5:1 to 50:1, (where the ratio of the volume of gas ($Q_g$) to the volume of liquid ($Q_l$) is determined at the desired reaction temperature and pressure).

21. A process as claimed in claim 16 wherein the injector-mixing nozzle is executed as a conduit having an inlet for the suspension and an outlet for the mixture of suspension and synthesis gas wherein a high shear pumping means is located in the conduit within 1 metre of the outlet of the conduit and synthesis gas is injected into the conduit immediately upstream or downstream of the high shear pumping means.

22. A process as claimed in any one of claim 3 wherein the gas bubbles have diameters in the range of from 1 μm to 10 mm.

23. A process as claimed in claim 3 wherein the gas voids coalesce to form larger gas voids or fragment to form smaller gas voids over a time period of up to 50 ms.

24. A process as claimed in claim 1 wherein suspension is withdrawn from the reactor vessel and is at least in part recycled to a high shear mixing zone(s) via an external conduit.

25. A process as claimed in claim 24 wherein the suspension which is recycled to the high shear mixing zone(s) is cooled outside of the high shear mixing zone(s) and the reactor vessel to a temperature which is 1 to 30° C. below the temperature of the suspension in the reactor vessel by means of an external heat exchanger located on the external conduit.

26. A process as claimed in claim 1 wherein the suspension is cooled within the reactor vessel by means of an internal heat exchanger.

27. A process as claimed in claim 25 wherein additional cooling is provided by introducing at least one vaporizable low boiling liquid hydrocarbon into the high shear mixing zone(s) and/or the reactor vessel and/or any external conduit.

28. A process as claimed in claim 1 wherein a gas cap is present in the top of reactor vessel above the level of suspension.

29. A process as claimed in claim 28 wherein the high shear mixing zone(s) discharge into the reactor vessel either above or below the level of suspension in the reactor vessel.

30. A process as claimed in claim 29 wherein the high shear mixing zone(s) are submerged below the level of the suspension in the reactor vessel and the synthesis gas is fed to the high shear mixing zone(s) via a gas line which passes through the walls of the reactor vessel and communicates with an inlet of the high shear mixing zone(s).

31. A process as claimed claim 24 wherein the suspension is recycled to the high shear mixing zone(s) through the external conduit via a slurry pump wherein the power input of the slurry pump is equivalent to an energy dissipation rate of at least 0.5 kW/m$^3$, based on the total volume of slurry in the system.

32. A process as claimed in any of claims 1 and 24 wherein the high shear mixing zone(s) are situated at or near the top of the reactor vessel and the suspension is removed from the reactor vessel at its bottom.

33. A process as claimed in claim 31 wherein the ratio of the volume of the external conduit to the volume of the reactor vessel, (excluding the volume of any external heat exchanger), is in the range of 0.005:1 to 0.2:1.

34. A process as claimed in claim 31 wherein up to 50% by volume of the hydrogen component of the synthesis gas and/or up to 50% by volume of the carbon monoxide component of the synthesis gas is introduced into the external conduit.

35. A process as claimed in claim 2 wherein the kinetic energy dissipation rate in the high shear mixing zone is in the range of from 0.5 to 5 kW/m$^3$.

36. A process as claimed in claim 4 wherein the volumetric mass transfer rate is in the range of 25 to 1000 kg-moles/H of carbon monoxide transferred per m$^3$ of suspension.

37. A process as claimed in claim 4 wherein the volumetric mass transfer rate is in the range of 5 to 100 kg-moles/h of carbon monoxide transferred per m$^3$ of suspension.

38. A process as claimed in claim 7 wherein the average residence time of the liquid component of the suspension in the reactor vessel is in the range of from 1 to 30 hours.

39. A process as claimed in claim 8 wherein the gas hourly space velocity (GHSV) is in the range 2000 to 15000 at normal temperature and pressure (NTP) based on the feed volume of synthesis gas at NTP.

40. A process as claimed in claim 10 wherein the system comprises up to 10 to 50 high shear mixing zones which project through the walls of a single reactor vessel or are located within a single reactor vessel.

41. A process as claimed in claim 14 wherein the high shear mixing zone(s) are angled at an angle of less than 20° relative to the longitudinal axis of the reactor vessel.

42. A process according to claim 14 wherein the high shear mixing zone(s) are angled at an angle of less than 10° relative to the longitudinal axis of the reactor vessel.

43. A process as claimed in claim 15 wherein the volume of suspension present in the high shear mixing zone(s) is less than 10% of the volume of suspension present in the remainder of the reactor system.

44. A process as claimed in claim 18 wherein the pressure drop of the suspension over the venturi nozzle(s) is in the range of from 2 to 15 bar and wherein the ratio of the volume of gas ($Q_g$) to the volume of liquid ($Q_l$) passing through the venturi nozzle(s) is in the range 1:1 to 5:1, where the ratio of the volume of gas ($Q_g$) to the volume of liquid ($Q_l$) is determined at the desired reaction temperature and pressure.

45. A process according to claim 20 wherein the pressure drop of gas over the nozzle(s) is in the range 3 to 100 bar, the pressure drop of suspension over the nozzle(s) is in the range of from 4 to 15 bar and the ratio of the volume of gas ($Q_g$) to the volume of liquid ($Q_l$) passing through the gas blast nozzle(s) is in the range 1:1 to 10:1, where the ratio of the volume of gas ($Q_g$) to the volume of liquid ($Q_l$) is determined at the desired reaction temperature and pressure.

46. A process according to claim 22 wherein the gas bubbles have diameters in the range of from 30 $\mu$m to 3000 $\mu$m.

47. A process as claimed in claim 22 wherein the gas bubbles have diameters in the range of from 30 $\mu$m to 300 $\mu$m.

48. A process as claimed in claim 31 wherein the suspension is recycled to the high shear mixing zone(s) through the external conduit via a slurry pump wherein the power input of the slurry pump is equivalent to an energy dissipation rate of at least 0.5 to 10 kW/m$^3$, based on the total volume of slurry in the system.

* * * * *